United States Patent [19]

Vilasi

[11] Patent Number: 5,647,358
[45] Date of Patent: Jul. 15, 1997

[54] EXPANDABLE INTER VIVOS TUBE

[76] Inventor: Joseph Vilasi, S. Shores Condo Unit 704 5635 A1A South, Melbourne Beach, Fla. 32951

[21] Appl. No.: 618,577

[22] Filed: Mar. 20, 1996

[51] Int. Cl.⁶ .................................................. A61M 16/04
[52] U.S. Cl. .......................... 128/207.14; 128/DIG. 20; 128/DIG. 25; 623/11; 138/156; 138/157
[58] Field of Search ........................ 128/207.14, 207.15, 128/200.26, DIG. 20, DIG. 25; 604/96, 99, 105; 623/1, 11, 9, 12; 138/156, 158, 160, 162, 167, 157

[56] References Cited

U.S. PATENT DOCUMENTS

| | | | |
|---|---|---|---|
| 3,968,800 | 7/1976 | Vilasi . | |
| 4,084,066 | 4/1978 | Gillemot | 138/158 |
| 4,219,051 | 8/1980 | D'Haeyer | 138/168 |
| 4,379,473 | 4/1983 | Kunze | 138/156 |
| 4,518,448 | 5/1985 | Henry et al. | 138/158 |
| 4,722,335 | 2/1988 | Vilasi . | |
| 4,740,207 | 4/1988 | Kreamer | 623/1 |
| 4,827,925 | 5/1989 | Vilasi . | |
| 5,192,307 | 3/1993 | Wall | 623/1 |
| 5,342,387 | 8/1994 | Summers | 606/198 |

OTHER PUBLICATIONS

"Clinical Anesthesia", 1989 Edition, J.B. Lippincott Company, edited by Paul Barsah, M.D., Bruce Cullen, M.D. and Robert Stoelting, M.D.

*Primary Examiner*—V. Millin
*Assistant Examiner*—Robert N. Wieland
*Attorney, Agent, or Firm*—Alfred M. Walker

[57] ABSTRACT

A flexible expandable inter vivos tube includes at least one arched segmented portion and at least one positioning mechanism, the at least one arched segmented portion and at least one positioning mechanism forming a flexible closed longitudinally extending tube, preferably an endotracheal tube for introduction of oxygen and other anesthetic gases from a source thereof into the lungs of a surgical patient or similar mammal. The positioning mechanism is preferable an H-shaped connector having at least one cul-de-sac receptacle cavity for variable slidable movement of at least one tapered tongue free end portions of the at least one arched segment therein. To move the at least one tongue portion within the at least one cul-de-sac receptacle cavity, fluid is introduced into at least one longitudinally extending lumen running mostly along the longitudinal axis of the flexible expandable inter vivos tube, so that the hydraulic pressure moves the at least one tongue portion away from an inner rib of said at least one H-shaped connector, thereby expanding the circumference and diameter of the flexible inter vivos tube. The flexible expandable inter vivos tube, such as an endotracheal tube, anchors reversibly within a body cavity, such as a trachea. Thereby, the inter vivos tube can be optimally positioned in the body cavity, such as the trachea without interfering with the tissues of the body cavity.

23 Claims, 8 Drawing Sheets

EXPANDABLE INTER VIVOS TUBE

FIELD OF THE INVENTION

The present invention refers to an expandable tube for inter vivos use in surgery, such as an expandable endotracheal tube, preferably for performing surgery or for replacement of vessels within the human body during medical surgery, or within mammals during veterinary surgery.

BACKGROUND OF THE INVENTION

Inter vivos tubes, such as endotracheal tubes, are used to provide gases to the lungs during surgery. The endotracheal tube is inserted into the trachea with its distal tip advanced halfway toward the tracheal bifurcation to provide gases, such as oxygen and anesthetics. The exposed portion of the endotracheal tube is then firmly taped to the patent's face to prevent undesirable movement.

To align the position of the prior art endotracheal tube, the inflatable cuff balloon, at the distal end of the endotracheal tube, is inflated to correspond to the inner diameter of a portion of the trachea, thereby centering or otherwise positioning the endotracheal tube within the trachea. The cuff balloon, however, does not completely obstruct the entire trachea, only the portion where it is anchored. When the cuff balloon is inflated, confirmation of the tube's contact within the trachea is achieved, and delivery of anesthetic gases is performed.

Because of various sized endotracheal tubes, it is preferable to at least make the outer diameter of the endotracheal tube to be closely proximate to the size of the glottis, or opening between the vocal cords, for selective positioning of the endotracheal tube at a predetermined location. Therefore, various sized tubes are used, and the anesthesiologist or nurse anesthetist must choose from a variety of sized tubes to insert.

Present day endotracheal tubes vary in size and are numbered according to internal diameter (ID). For example, for children, tubes are measured of about 3.5–7 mm internal diameter, and from 7–11 mm for an adult.

The internal diameter in women varies in general from 7.0 to 8.5 mm ID and in men from 8 to 10 mm ID. Therefore, the endotracheal tube size selected for each patient is empirically selected by the anesthesiologist based on the patent's gender, age and size.

Ideally, the endotracheal tube should approximate as closely as possible the glottic size of the patient. Since there is no way to estimate the glottic size prior to the administration of anesthesia, in the existing prior art endotracheal tubes, a distal inflatable cuff is incorporated into the present day endotracheal tube which, when inflated, compresses the tracheal wall, thus creating a closed circuit between the endotracheal tube inflow from the anesthesia machine and outflow from the patent's lung to the exhalation valve.

Furthermore, as noted in "Clinical Anesthesia", 1989 Edition, J. B. Lippincott Company, edited by Paul Barash, MD, Bruce Cullen, MD, and Robert Stoelting, MD, it is stated:

"Endotracheal tube resistance varies inversely with the tube size. Each millimeter decrease in tube size is associated with an increase in resistance of 25–100%. The work of breathing parallels changes in resistance. A 1 mm decrease in tube size increases the work of breathing 34–154%, depending on the ventilatory pattern".

Therefore, in existing prior art tubes, the internal diameter is small, and the only large portion is the external cuff balloon. This makes it harder for a surgical patient to breathe through the small internal diameter of the existing endotracheal tubes.

Applicant's prior U.S. Pat. Nos. 3,968,800 dated Jul. 13, 1976 and 4,827,925 dated May 9, 1989 describe an adjustable endotracheal tube which is complex to expand, and which does not have flexibility in being adapted to varying sized tracheas of different patients. Applicant's other prior U.S. Pat. No. 4,722,335 dated Feb. 2, 1988 discloses an expandable endotracheal tube including two overlapping curved segments, which when joined together form a closed tube. However, the configuration may be conceptually possible but in practical terms, difficult to construct and maintain at present prices.

OBJECTS OF THE INVENTION

It is therefore an object of the present invention to provide a flexible, expandable endotracheal tube which expands its internal diameter at the glottic region of the trachea, to make breathing easier for a surgical patient.

Another object of the flexible, expandable inter vivos tube of the present invention is to vary the size of the internal diameter (ID) of an endotracheal tube from size 7 mm ID to 11 mm ID in order to reach the glottic size of the patient without the intervention of a distal inflatable cuff. With the present invention, the distal cuff is unnecessary and one size endotracheal tube would fit most all adult patients. The present invention is especially useful in nasotracheal intubations where normally an even smaller internal diameter tube would be selected by the anesthesiologist.

It is also an object of the present invention to provide an endotracheal tube that maintains the same wall thickness throughout.

It is yet another object of the present invention to provide an endotracheal tube having an internal diameter that remains consistent from it's proximal to distal end.

Another object of the present invention is to provide a vessel for administration of anesthesia during surgery by means of a flexible expandable tube that can be positioned correctly, such as a flexible expandable endotracheal tube which can be inserted without interrupting gas flow and/or organ activity of a surgical patient.

In another embodiment, the vessel can be an artificial flexible expandable vessel, such as an artificial vessel, such as a segment blood vessel portion to replace clogged arteries, or as a permanent catheter duct for providing fluids to or from the body.

It is also an object of the present invention to improve over the disadvantages of the prior art.

SUMMARY OF THE INVENTION

The basic concept of the present invention is to equip an inter vivos vessel, such as an endotracheal tube or artificial blood vessel with a positioning mechanism which preferably is activated from the proximal end of the vessel and allows exact positioning and reversible anchoring within a body cavity, such as the trachea.

In the endotracheal tube embodiment, exact positioning and anchoring provide the conditions to provide anesthetic gases at the target, namely to the bronchial tubes and ultimately the lungs.

By means of the preferred embodiment of the present invention, the endotracheal tube can be anchored in the internal diameter of a body cavity, such as the trachea. The tube is expanded in size by means of an axially and longitudinally extending H-shaped element, having inserted within the opposite free ends thereof two corresponding free ends of the main body of the endotracheal tube, which comprises a flexible longitudinally extending cylinder, interrupted by a longitudinally extending incision running the length thereof. The two free edges of the flexible cylindrical body are engagable within corresponding free ends of the H-shaped element, which is curved to complete the circumference of the flexible expandable endotracheal tube.

Moreover, upon extubation of the new endotracheal tube of the present invention, retraction of the diameter of the tube is not required. In contrast, in prior art endotracheal tubes, the cuff balloon must be completely deflated to prevent damage to the vocal chords during extubation after surgery.

The free ends of the flexible interrupted cylindrical tube are axially and longitudinally displaced away from each other so that the internal diameter of the endotracheal tube is expanded to anchor the tube within a body cavity, such as the trachea. One or more lumens are used to provide fluid or air within the selected longitudinally extending lumens, to spread the free ends of the interrupted cylindrical tube away from each other, thereby increasing the internal diameter thereof.

In another embodiment of the present invention, two H-shaped elements are provided at opposite sides of the cylindrical body which is broken into two curved longitudinally extending segments. By axially shifting the segmented arches away from each other at the free ends thereof, the segmented arches are expanded so that the size of the endotracheal tube is increased to anchor to the surface of the trachea during insertion. The segmented arches can be spread by injecting gas, such as air or fluid, such as saline fluid, into corresponding lengthwise extending lumens to increase the space between the segmented arches and thereby secure the endotracheal tube in place.

According to a modified embodiment of the invention, the free ends of one side of the cylindrical body, or segmented arch, can be moved, and the opposite side is firmly attached inside the other free end of the H-shaped element. By means of the self-acting spreading of the endotracheal tube during insertion, the position of the endotracheal tube is advanced so that controlled anesthesia can be performed.

In summary, the prior art uses a local, inflatable balloon at the distal portion of an endotracheal tube, which may damage the vocal chords of the patient, if not properly installed and will narrow the patient's air way at the vocal chord level. In contrast, the endotracheal tube of the present invention expands uniformly along its axial length, as fluid, such as saline solution, is pumped from a syringe into expansion lumens which comprise fluid receptacles, and the filling of which causes the radial expansion of the present invention endotracheal tube longitudinally along its length.

BRIEF DESCRIPTION OF THE DRAWINGS

The present invention is described in more detail using the preferred embodiment depicted schematically in the attached drawings, wherein.

DETAILED DESCRIPTION OF THE DRAWINGS

Figure 14:
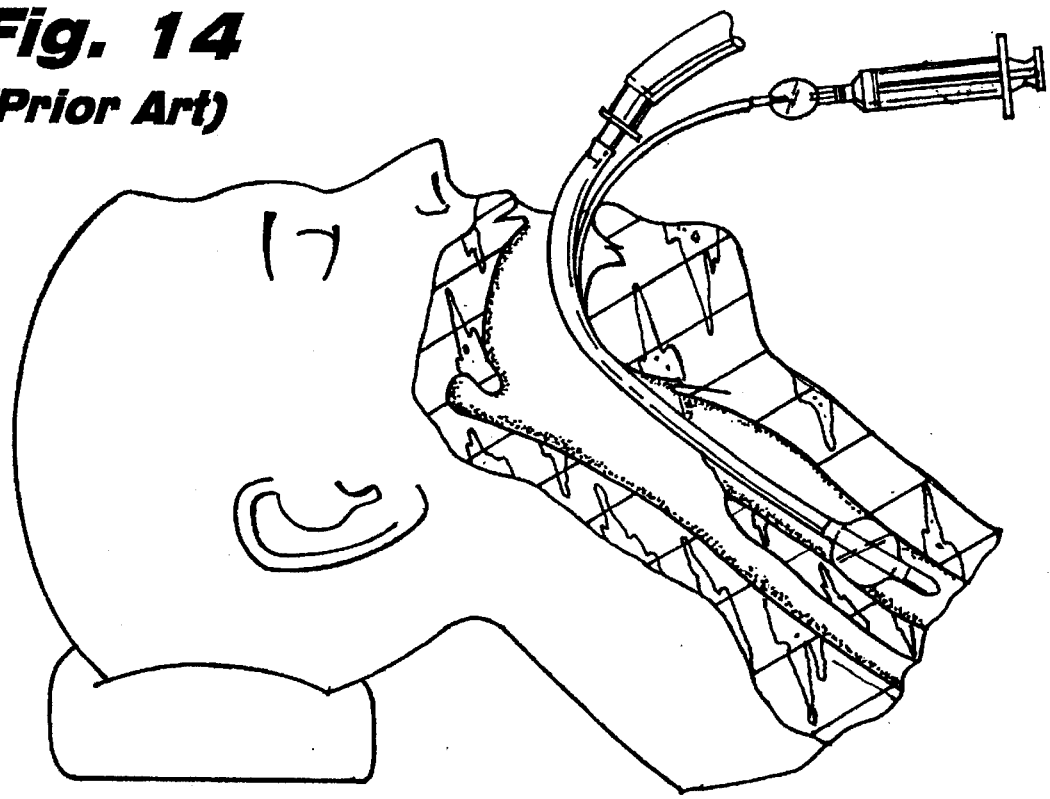
FIG. 14 is a partial elevational sectional view of a prior-art endotracheal tube installed in a patient's throat; and, FIG. 15 is a partial elevational sectional view of the preferred embodiment of the present invention for a endotracheal tube installed in a patient's throat.

FIG. 14 shows a prior art endotracheal tube, having a non-expandable patient-breathing conduit. The prior art endotracheal tube is secured in place within the trachea of the patient by having a balloon, which is circumferentially attached to a distal portion of the tube inflated with air. Once the distal balloon is inflated, its expansion causes a friction-fit within the trachea, anchoring and securing the entire endotracheal tube within the trachea, so as to prevent inadvertent slippage or removal of the tube, with resulting adverse patient consequences. The prior art balloon is inflated by activating an external fluid syringe which pumps air through a conduit called a lumen, which conduit parallels the endotracheal breathing conduit, the lumen conveying air to the anchoring balloon.

Figure 15:
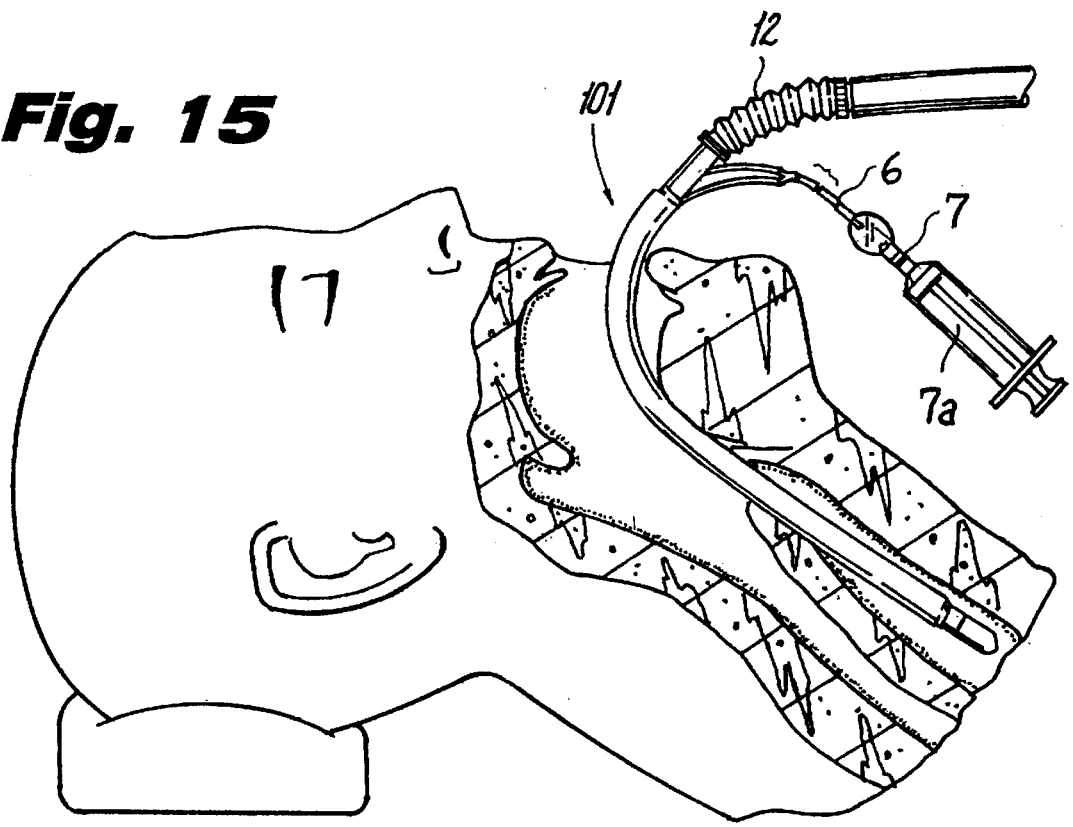

FIG. 15 shows the present-invention endotracheal tube 101, shown inserted within the trachea of a patient. The endotracheal tube 101 is shown in contact with the patient's glottis region of the upper portion of the trachea. Glottis aperture diameter is indicated by opposing arrows in the drawing FIG. 15. Syringe 7a provides fluid through port 7 and into delivery tube 6 a desired volume of inflation fluid. Appropriate desired medical gases, such as air, oxygen or anesthesia gases are introduced to the patient through flexible tube coupling 12 which connects gas supply tubing to the endotracheal tube 101 of the present invention.

FIGS. 1 through 9 show an embodiment of the endotracheal tube 1 of the present invention which includes circumferentially spaced-apart arched segments 2 and 2a separated from each other by a pair of positioning mechanisms 3 and 3a. Although preferably the positioning mechanism is preferably at least one H-shaped connector, as shown in FIGS. 10–13, it is known that other configurations may also be used.

Figure 1:
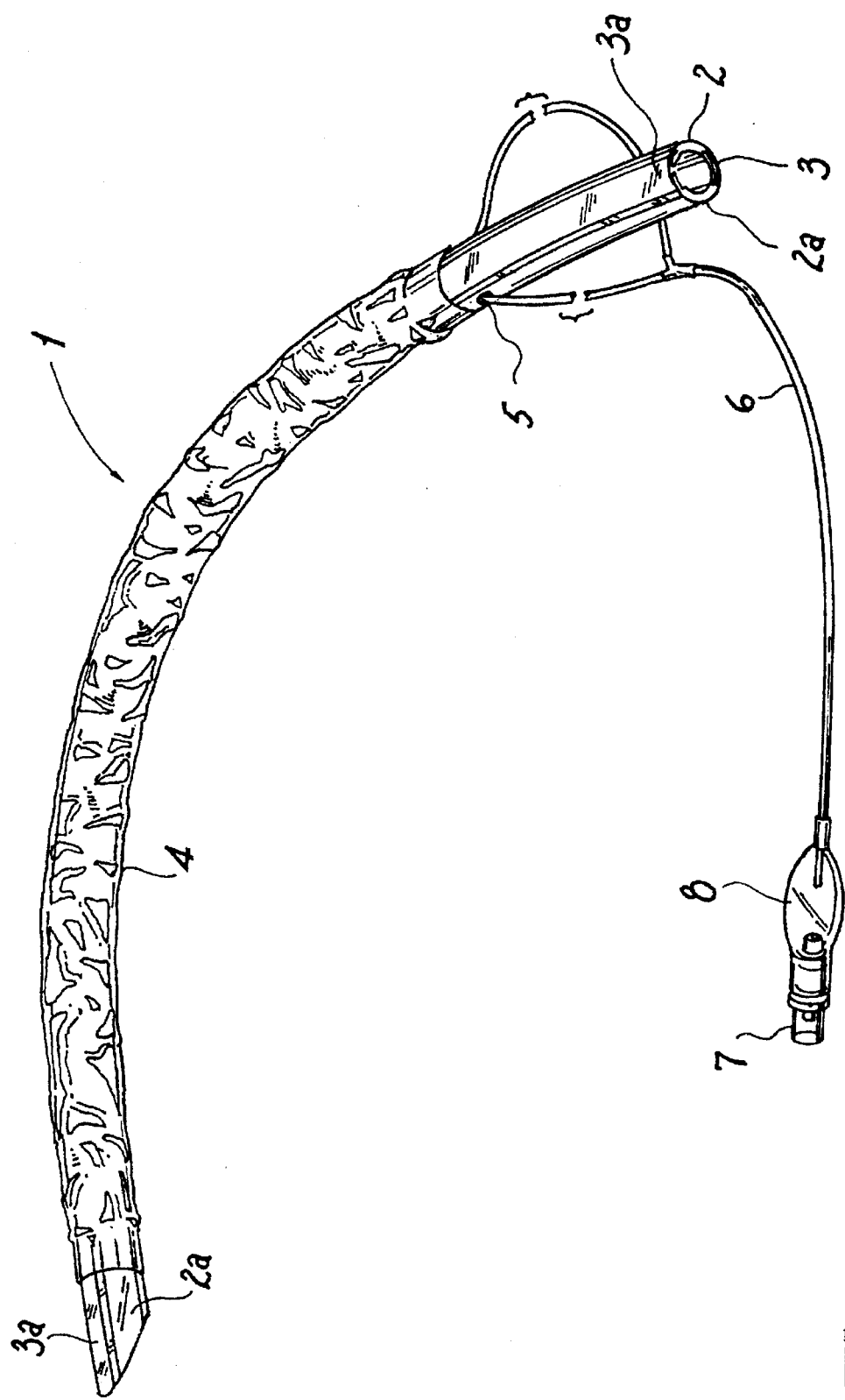
FIG. 1 is an overall perspective view of an unexpanded tube of one embodiment of the present invention.
Figure 2:
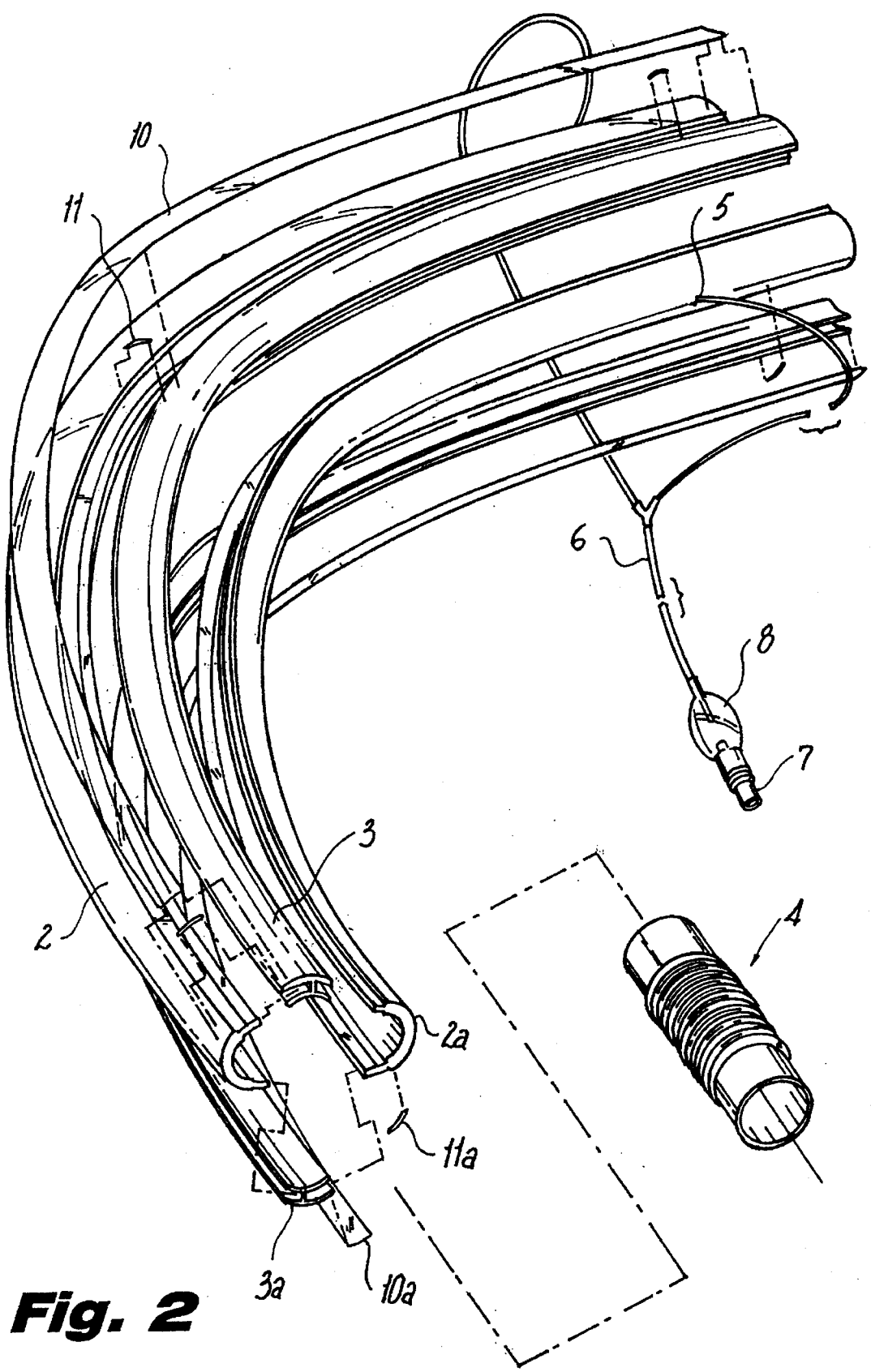
FIG. 2 is an exploded perspective of the embodiment as in FIG. 1.
Figure 3:
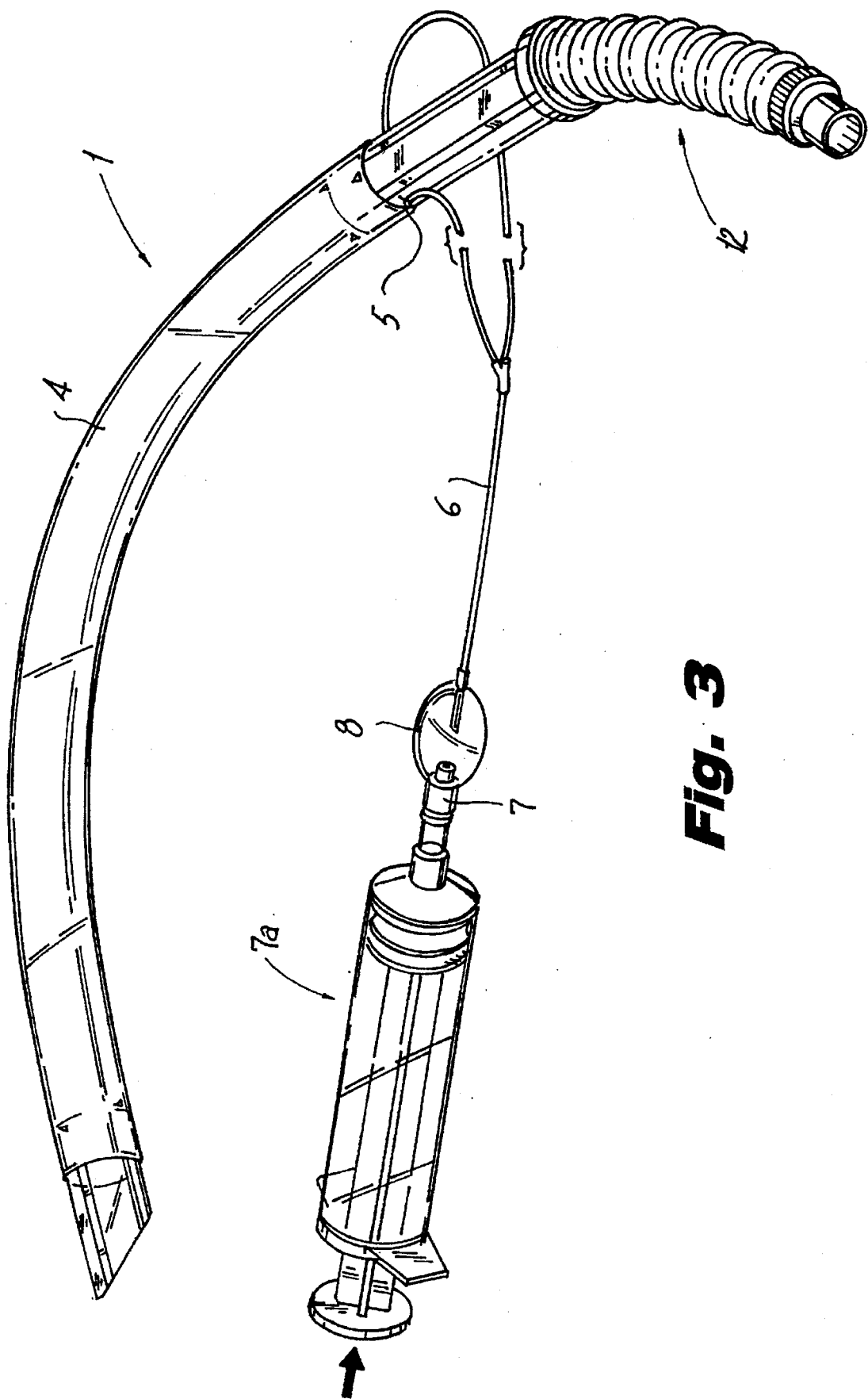
FIG. 3 is an overall perspective view of the expanded tube as in FIG. 1.
Figure 4:
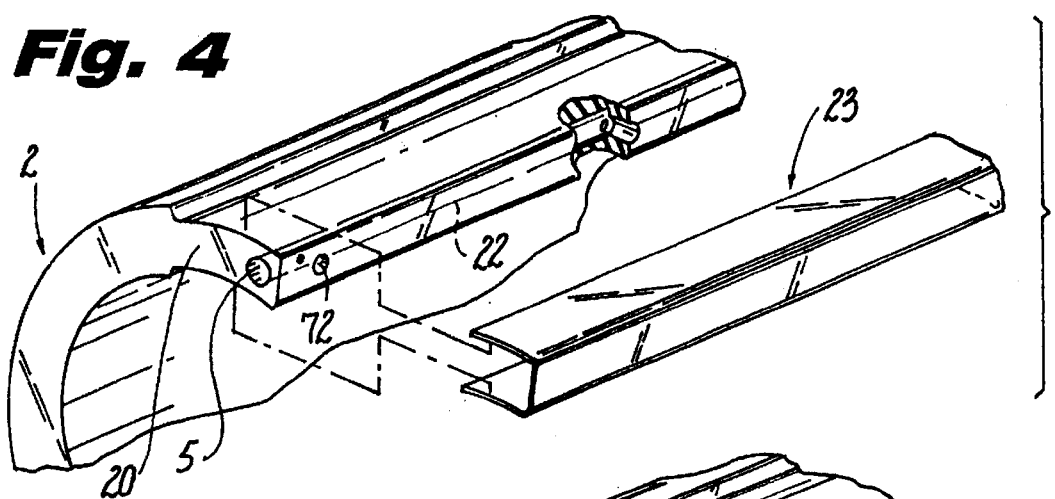
FIG. 4 is an exploded perspective view of a partial wall portion showing an inflation lumen and a distensible inflation material edge.
Figure 5:
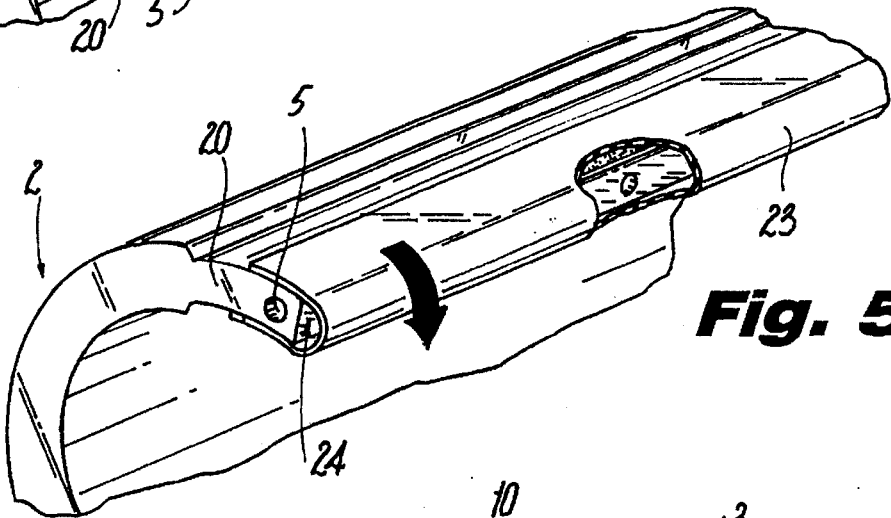
FIG. 5 is a perspective view of the partial wall portion as in FIG. 4, shown expanded with fluid.
Figure 6:
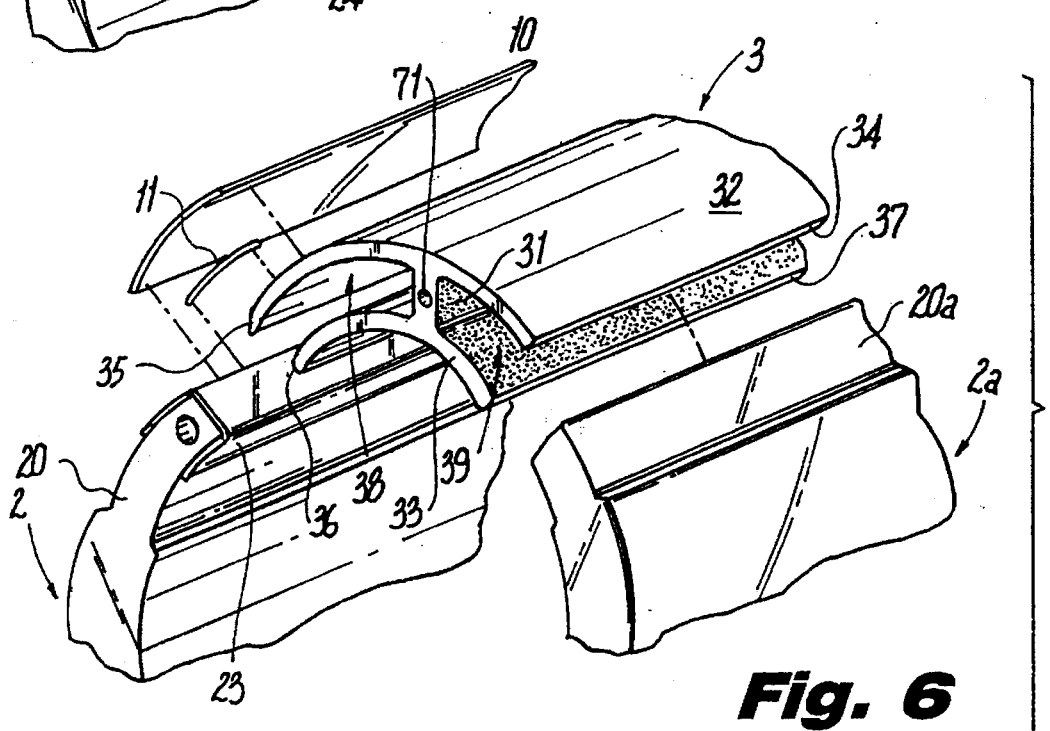
FIG. 6 is an exploded view of the wall components of the embodiment as in FIG. 1, shown attaching to an H-Shaped extrusion element, with expansion-restricting items including a filament and expandable sheet cover portion.
Figure 7:
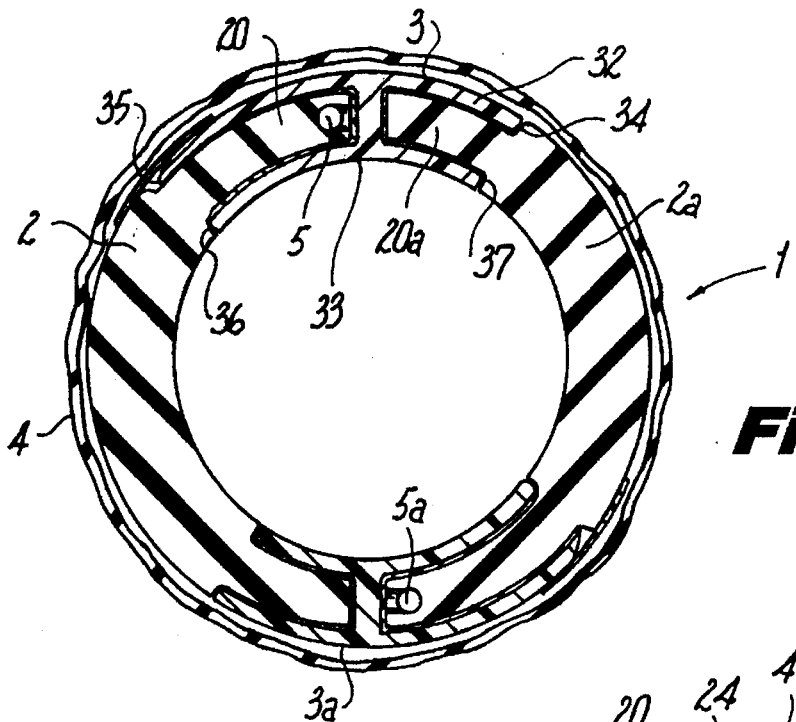
FIG. 7 is a cross-sectional view of the embodiment as in FIG. 1.
Figure 8:
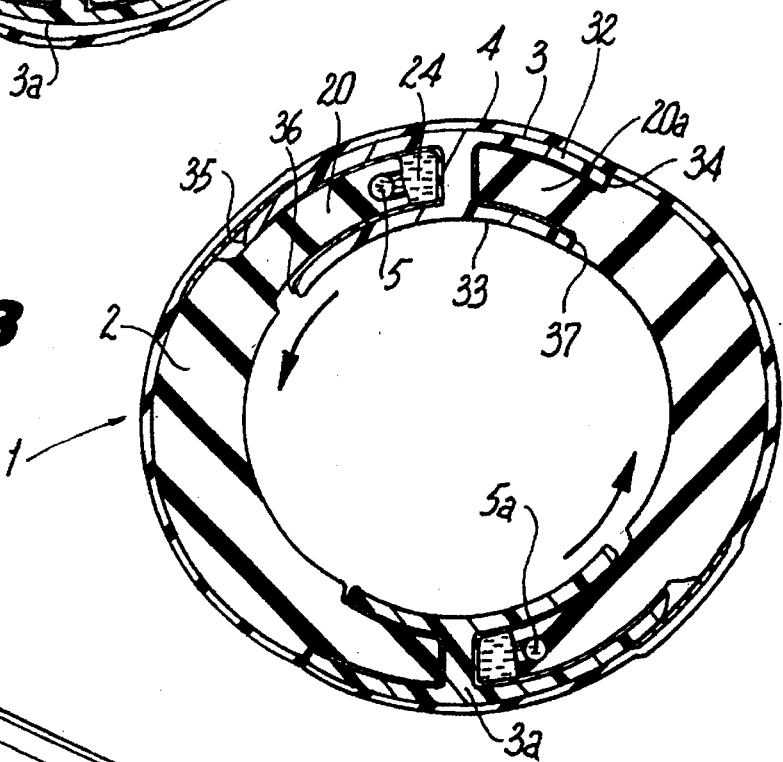
FIG. 8 is a cross-sectional view of the embodiment as in FIG. 3.
Figure 9:
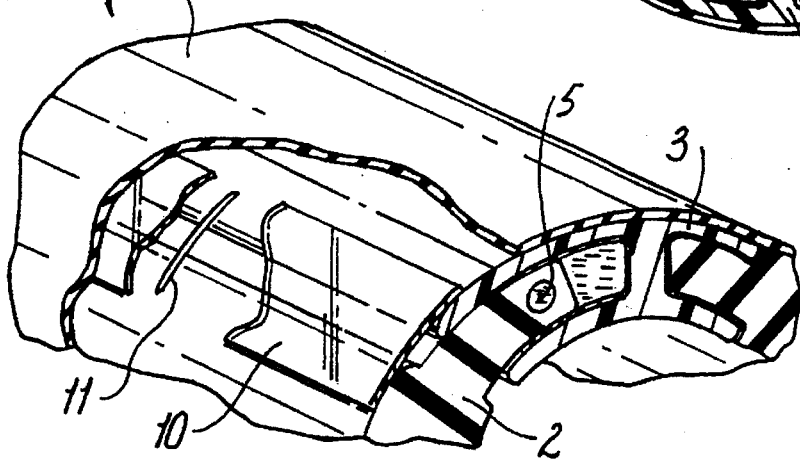
FIG. 9 is a close up perspective cut-away view showing expansion restricting elements.
Figure 10:
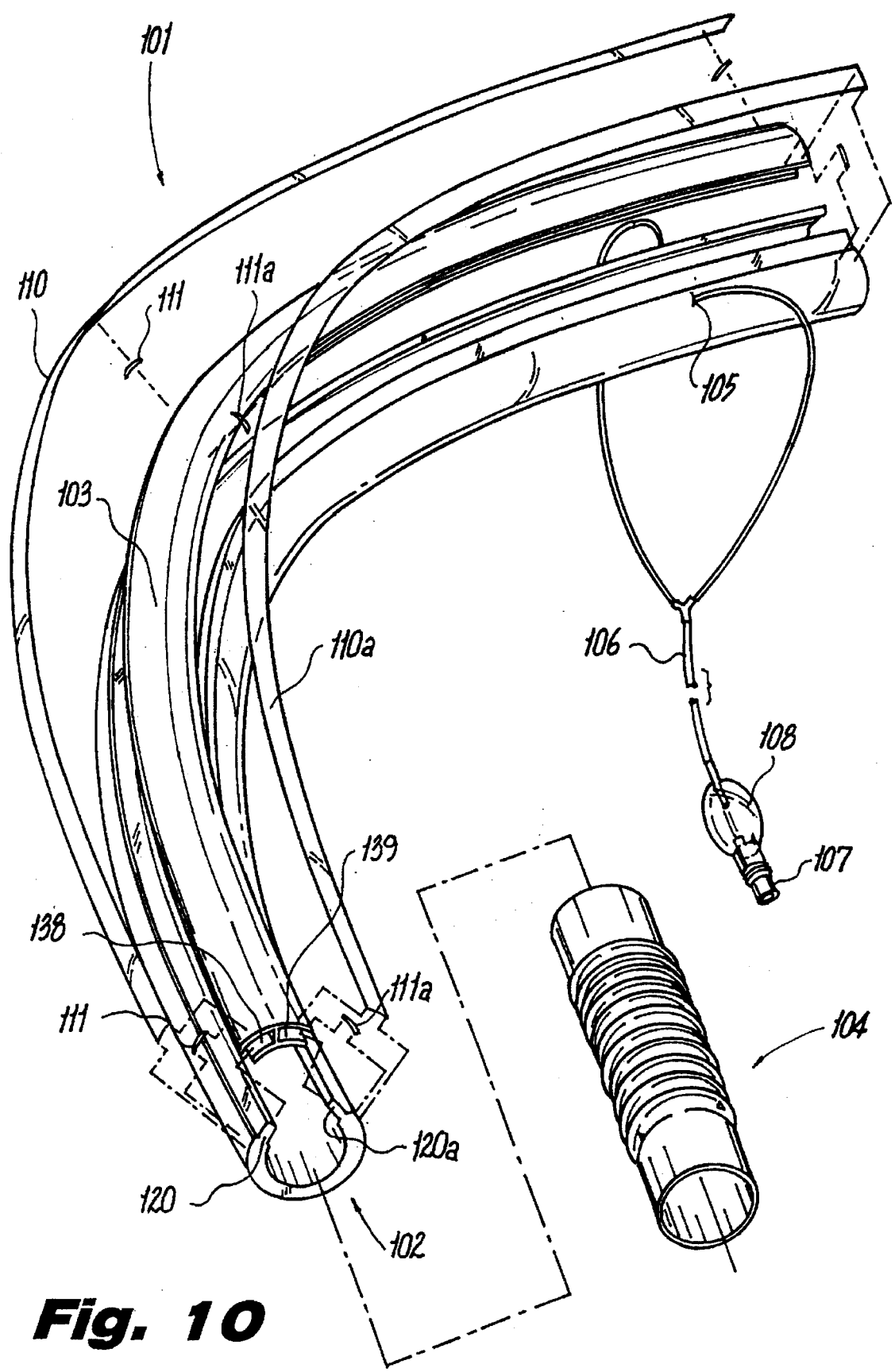
FIG. 10 is an exploded perspective view of an alternate embodiment with a single H-Shaped extrusion element.

Flexible expandable inter vivos tube is covered by a tissue friendly expandable material, such as a latex cover 4, which is shown in an expanded position in FIG. 1 over endotracheal tube 1. In the exploded view in FIG. 2, latex cover 4 is shown in the unexploded position before insertion over endotracheal tube 1.

Furthermore, in contrast to the single H-shaped connector shown in FIGS. 10–13, in FIGS. 1–9, the positioning mechanism comprises a plurality, such as a pair of H-Shaped connectors 3 and 3a, the H-Shaped connectors 3 and 3a comprising an integral portion of endotracheal tube wall of endotracheal tube 1.

In FIGS. 1–9, the H-Shaped connectors 3 and 3a are arranged circumferentially opposite each other, at equal angles to each other along a circumference of said flexible expandable inter vivos tube 1.

Likewise, in FIGS. 1–9, arched segments 2 and 2a are also arranged circumferentially opposite each other, at equal angles to each other along a circumference of said flexible expandable inter vivos tube 1.

The H-Shaped connectors 3 and 3a include a rib 31, which rib 31 comprises the cross-bar of the "H" in the H-Shape, and the H-Shape also includes circumferentially curved wings, said H-Wings 32 and 33 roughly corresponding to the vertical strokes of a traditional letter "H" but in the present invention the H-Wings comprise cul-de-sac receptacle cavities 38 and 39 for variably receiving, in tongue-in-groove-like fashion, the tapered free end tongue portions 20 and 20a of arched tube segments 2 and 2a. The H-Wings 32 and 33 have respective end portions which are free ends 34 and 35, and 36 and 37, respectively. Outer curved wing 32 is longer than inner curved wing 33 to accommodate an increase in circumference.

Rib 31 connects the curved wings 32, 33 of each h-shaped connector 3, 3a, for providing rigidity and structural integrity for the endotracheal tube 1, the rigidity having therewith sufficient flexibility to enable the endotracheal tube to be inserted into the trachea of the patient and to conform to the patient's airway, while retaining sufficient rigidity to permit a medical worker to position and to insert the tube against anatomical resistance of the patient's throat and airway structures.

Rib 31 may also include longitudinal conduit 71 for accepting a fiber optic cable for view-scope enablement.

Tongues 20 and 20a are each provided with a distensible membrane 23, which membranes 23 are fused to the external and internal extremities of tongues 20 and 20a, wherein the free end of membranes 23 are distensible. Moreover, the proximal and distal ends of membranes 23 are fused to prevent leakage of fluid therefrom. Membranes 23 are variably distensible and retractable in response to variable pressure from pumped (as by syringe) hydraulic fluid, such as saline solution, the membrane 23 providing a piston seal so as to permit tongues 20 and 20a to function slidably as a piston within H-Wing receptacles 38 and 39.

Tongues 20 and 20a are normally in a retracted position, providing endotracheal tube 1 with a minimum diameter.

The diameter of endotracheal tube 1 increases when tongues 20 and 20a are forced circumferentially apart by entrance of pumped hydraulic fluid into the respective spaces 24 between tongues 20 and 20a and distensible sealed membranes 23, causing distention of membranes 23.

As membranes 23 distend, tongues 20 and 20a are forced by the mechanical pressure resulting from the hydraulic pressure to move circumferentially and axially apart, and away from the rib 31.

Hydraulic fluid is conducted at a proximal end of said flexible expandable inter vivos tube to the spaces 24 between tongues 20 and 20a and distensible membranes 23 through at least one longitudinal lumen conduit 5 and then exiting from lumen 5 through axial apertures 72 providing access for the hydraulic fluid from lumen 5 into the spaces 24 between tongues 20 and 20a and membranes 23.

Arched segments 2 and 2a are preferably provided with at least one tapered tongue 20 and 20a for fitting slidably into the receptacles comprising H-Wings 32 and 33. Moreover, tapered tongues 20 and 20a each have a first thickness less than a corresponding second thickness of said arched segments 2 and 2a. The second thickness of said arched segments 2 and 2a is approximately equal to a third thickness of connectors 3 and 3a, so that insertion of tongues 20 and 20a within cul-de-sac receptacle cavities 38 and 39 is stopped and limited in movement by contact of arched segments 2 and 2a against connectors 3 and 3a and by contact against ribs 31 of H-shaped connectors 3 and 3a.

As also shown in FIGS. 1 through 9 inclusive, there is provided inlet 7 for injection of saline solution or air from a syringe (not shown). A pilot balloon 8 acts as a valve to direct or control the flow of fluid through catheter tube 6 into longitudinally extending lumen 5, which extends along the length of endotracheal tube 1, for introduction of fluid therethrough for expanding the diameter of endotracheal tube 1 by means of fluid movement within fluid chamber space 24, causing the outward movement of free ends of arched segments 2 and 2a within cavities 38 and 39 provided between H-Wings 32 and 33 of H-Shape connectors 3 and 3a, by fluid pressure inflation.

To seal the joint between arched segments 2 and 2a and H-shaped members 3 and 3a, cover sheets 10 and 10a are provided fused onto H-shaped connectors 3 and 3a, as well as to the widest parts of arched segments 2 and 2a. To prevent over-expansion of endotracheal tube 1, transversely extending reinforcement filaments 11 and 11a are provided beneath cover sheets 10 and 10a. Cover sheets 10 and 10a provide assistance in maintaining the integrity of the tube and for smoothing out any irregularities that may occur when tube 1 is fully expanded. Filaments 11 and 11a are covered by cover sheets 10 and 10a and are fused to arched segments 2 and 2a and H-shaped connectors 3 and 3a.

Optionally, in an alternate embodiment, hydraulic fluid pumped into lumen 5 may enter fluid chamber space 24 through axial apertures 72, in the presence of other sealing means so that the hydraulic fluid exerts direct mechanical separating pressure between H wing walls receptacles 38 and 39 and tongues 20 and 20a.

FIGS. 10 through 13 show a preferred alternate embodiment having one interrupted arched segment 102 having tongue portions 120 and 120a which are slidably movable within H-Wing wall receptacles 138 and 139 of H-Shaped member 103. To seal the joint between arched segment 102 and H-shaped member 103, cover sheets 110 and 110a are provided. To prevent over-expansion, two or three transversely extending filaments 111 and 111a are provided beneath covers 110 and 110a.

Figure 11:
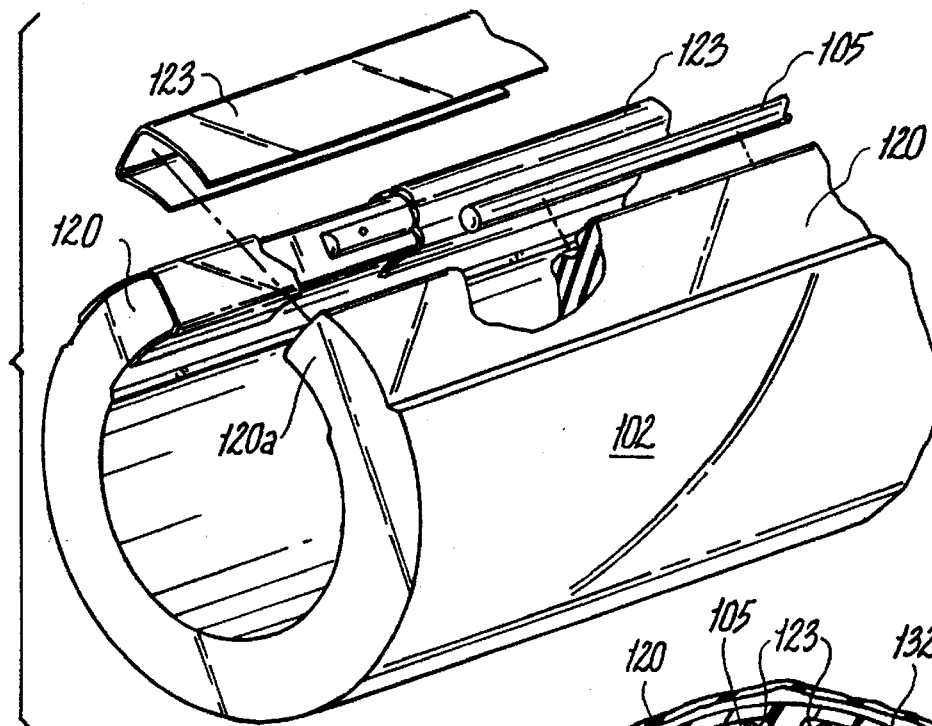
FIG. 11 is a close up perspective view of a wall unit with catheters which are fused at the free ends of the arched segment portions of the inter vivos tube of the present invention.
Figure 12:
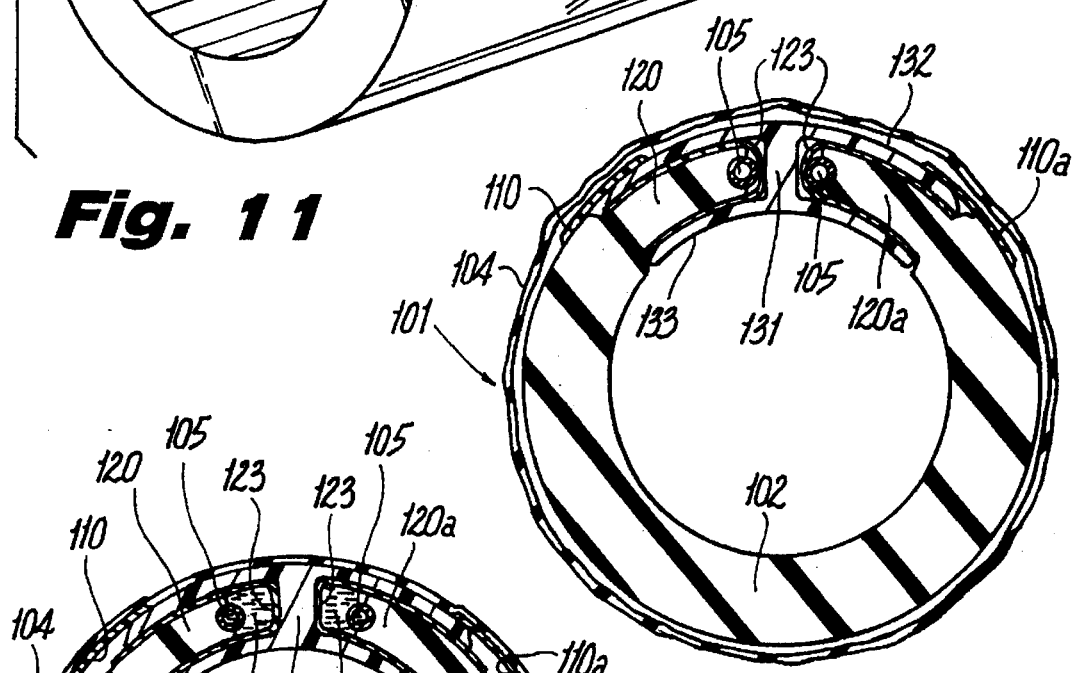
FIG. 12 is a cross sectional view of the tube as in FIG. 10 shown in an unexpanded state.
Figure 13:
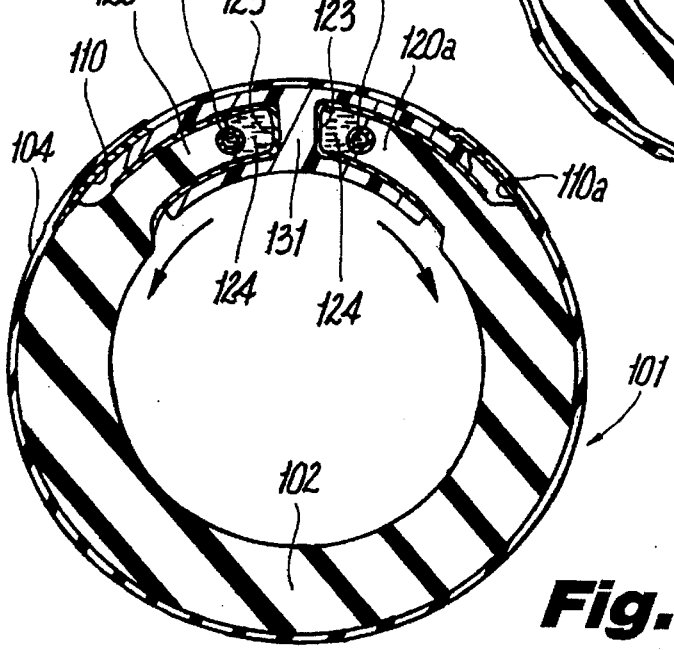
FIG. 13 is a cross sectional view of the tube as in FIG. 10 shown in an expanded state.

FIGS. 11 through 13 also show an alternate embodiment wherein a perforated catheter 105 is fused to tongues 120 and 120a. The catheter 105 is in turn enclosed within distensible membrane sheet 123 so fluid is introduced from catheter 105 into space 124 between membranes 123 and an end of tongues 120 and 120a.

The new endotracheal tube embodiments of inter vivos tubes 1 and 101 utilize the same semi-rigid plastic of present day tubes (polyvinylchloride or PVC) and are also disposable. Except for the "H"-shaped connectors 3 and 3a of new endotracheal tube, all other parts of the new endotracheal tube embodiments of inter vivos tubes 1 and 101 utilize present-day technology.

Therefore, the endotracheal tube embodiments of the present invention can be easily used in present day surgeries.

It is known that other modifications may be made to the present invention, without departing from the scope of the invention, as noted in the appended claims.

I claim:

1. A flexible expandable inter vivos tube, for insertion into a body cavity of a person or other mammal, comprising:

a flexible longitudinally extending tube interrupted by a cavity extending longitudinally along an exterior edge thereof;

said flexible longitudinally extending tube having a pair of free ends extending longitudinally along each side of said longitudinally extending cavity, and a longitudinally extending positioning mechanism, said longitudinally extending positioning mechanism circumferentially joining said free ends of said flexible longitudinally extending tube therein to form a closed tube, wherein said pair of free ends are slidably movably within said positioning mechanism, said pair of free ends are capable of being expanded and when expanded, cooperate with said positioning mechanism to expand the diameter of said inter vivos tube for reversibly anchoring said flexible expandable inter vivos tube within a body cavity without obstruction.

2. The flexible expandable inter vivos tube as in claim 1 wherein said positioning mechanism comprises a substantially H-shaped connector, said H-shaped connector having a pair of parallel wings joined by a common rib, said wings substantially corresponding to the vertical strokes of a traditional letter "H", said wings having a pair of cul-de-sac receptacle cavities therebetween, said pair of cul-de-sac receptacle cavities receiving, in tongue-in-groove-like fashion, said free ends of said flexible longitudinally extending tube.

3. The flexible expandable inter vivos tube as in claim 2 wherein said free ends of said flexible longitudinally extending tube are tapered tongues.

4. The flexible expandable inter vivos tube as in claim 2 wherein said flexible expandable inter vivos tube expands in diameter by hydraulic fluid pressure against said common rib of said H-shaped connector to move said tapered tongues within said cul-de-sac receptacle cavities for anchoring said flexible expandable inter vivos tube within a body cavity of the person or similar mammal.

5. The flexible expandable inter vivos tube as in claim 1 wherein said positioning mechanism runs along a longitudinal axis of said flexible expandable inter vivos tube.

6. The flexible expandable inter vivos tube as in claim 1 wherein said flexible expandable inter vivos tube expands its diameter radially to allow reversible and form fitting anchoring of said flexible expandable inter vivos tube within the body cavity of the person or similar mammal.

7. The flexible expandable inter vivos tube as in claim 1 wherein said flexible expandable inter vivos tube comprises at least one longitudinally extending arched segment.

8. The flexible expandable inter vivos tube as in claim 1 wherein said flexible expandable inter vivos tube comprises a plurality of longitudinally extending arched segments.

9. The flexible expandable inter vivos tube as in claim 1 wherein said positioning mechanism comprises at least one positioning mechanism.

10. The flexible expandable inter vivos tube as in claim 1 wherein said positioning mechanism comprises a plurality of positioning mechanisms.

11. The flexible expandable inter vivos tube as in claim 8 wherein said arched segments are arranged circumferentially at equal angles to each other.

12. The flexible expandable inter vivos tube as in claim 10 wherein said positioning mechanisms are arranged circumferentially at equal angles to each other.

13. The flexible expandable inter vivos tube as in claim 2 wherein the slidable movement of said tongues within said cul-de-sac receptacle cavities is variable.

14. The flexible expandable inter vivos tube as in claim 2 wherein said flexible expandable inter vivos tube comprises a flexible expandable endotracheal tube which expands in diameter to remain in contact with the glottis region of the trachea of the person or similar mammal.

15. The flexible expandable inter vivos tube as in claim 2 wherein said flexible expandable inter vivos tube comprises an artificial conduit vessel tube which expands in diameter to remain in contact within a conduit vessel of the person or similar mammal.

16. The flexible expandable inter vivos tube as in claim 15 wherein said artificial conduit vessel tube comprises an artificial blood vessel replacement segment.

17. The flexible expandable inter vivos tube as in claim 15 wherein said artificial conduit vessel tube comprises an artificial duct catheter segment.

18. The flexible expandable inter vivos tube as in claim 15 wherein expansion is activated from the proximal end of said flexible expandable inter vivos tube by insertion of a fluid within said longitudinal lumen to a space between said at least one tongue and said rib of said H-shaped connector.

19. The H-shaped connector as in claim 2 wherein said rib further comprises a fiber optic cable therein.

20. The flexible expandable inter vivos tube as in claim 2 further comprising at least one cover sheet covering a joint between said at least one arched segment and said at least one H-shaped connector.

21. The flexible expandable inter vivos tube as in claim 20 further comprising at least reinforcement filament placed under said cover sheet transversely to a longitudinal length of said cover sheet.

22. The flexible expandable inter vivos tube as in claim 1, wherein said flexible expandable inter vivos tube is covered by a tissue friendly expandable material.

23. The flexible expandable inter vivos tube as in claim 1, wherein said tissue friendly expandable material further comprises a latex cover.

* * * * *